US010342759B2

(12) United States Patent
Prinz

(10) Patent No.: US 10,342,759 B2
(45) Date of Patent: Jul. 9, 2019

(54) AQUEOUS OPHTHALMIC SOLUTION AND METHOD FOR TREATING DRY EYE SYNDROME

(71) Applicant: CROMA-PHARMA GESELLSCHAFT M.B.H., Leobendorf (AT)

(72) Inventor: Martin Prinz, Leobendorf (AT)

(73) Assignee: CROMA-PHARMA GESELLSCHAFT M.B.H., Leobendorf (AT)

( * ) Notice: Subject to any disclaimer, the term of this patent is extended or adjusted under 35 U.S.C. 154(b) by 0 days.

(21) Appl. No.: 15/308,797

(22) PCT Filed: May 4, 2015

(86) PCT No.: PCT/EP2015/059674
§ 371 (c)(1),
(2) Date: Nov. 3, 2016

(87) PCT Pub. No.: WO2015/169728
PCT Pub. Date: Nov. 12, 2015

(65) Prior Publication Data
US 2017/0224614 A1    Aug. 10, 2017

(30) Foreign Application Priority Data

May 7, 2014    (EP) ..................................... 14167381

(51) Int. Cl.
| | | |
|---|---|---|
| *A61K 9/00* | (2006.01) | |
| *A61K 9/08* | (2006.01) | |
| *A61K 31/715* | (2006.01) | |
| *A61K 47/10* | (2017.01) | |
| *A61K 47/02* | (2006.01) | |
| *A61K 47/26* | (2006.01) | |
| *A61K 47/18* | (2017.01) | |
| *A61K 47/38* | (2006.01) | |
| *B65D 65/40* | (2006.01) | |
| *A61K 51/06* | (2006.01) | |
| *A61K 47/61* | (2017.01) | |
| *A61K 47/24* | (2006.01) | |
| *B65D 81/26* | (2006.01) | |

(52) U.S. Cl.
CPC ............ *A61K 9/0048* (2013.01); *A61K 9/08* (2013.01); *A61K 31/715* (2013.01); *A61K 47/02* (2013.01); *A61K 47/10* (2013.01); *A61K 47/183* (2013.01); *A61K 47/24* (2013.01); *A61K 47/26* (2013.01); *A61K 47/38* (2013.01); *A61K 47/61* (2017.08); *A61K 51/06* (2013.01); *B65D 65/40* (2013.01); *B65D 81/266* (2013.01)

(58) Field of Classification Search
CPC ...... A61K 9/08; A61K 9/0048; A61K 41/715; A61K 47/02; A61K 47/20; A61K 47/24; A61K 47/26; A61K 47/38; A61K 47/183; A61K 31/715; B65D 65/40; B65D 81/266
USPC ........................................................... 514/54
See application file for complete search history.

(56) References Cited

U.S. PATENT DOCUMENTS

| | | | |
|---|---|---|---|
| 5,412,076 A | 5/1995 | Gagnieu | |
| 6,468,548 B1 * | 10/2002 | Kis ...................... | A61K 9/0048 424/400 |
| 2008/0093247 A1 * | 4/2008 | Han ..................... | A61K 9/0048 206/438 |

FOREIGN PATENT DOCUMENTS

| | | | |
|---|---|---|---|
| EP | 0551848 | 7/1993 | |
| EP | 1126881 | 8/2001 | |
| JP | 2000302803 | 10/2000 | |
| WO | WO 2008/077172 A2 * | 7/2008 | ............... A61K 8/46 |
| WO | WO2008077172 | 7/2008 | |
| WO | WO2008094675 | 8/2008 | |
| WO | WO2009032526 | 3/2009 | |
| WO | WO2009132226 | 10/2009 | |
| WO | WO2009132227 | 10/2009 | |
| WO | WO2009132228 | 10/2009 | |

OTHER PUBLICATIONS

Garhofer et al, Cataract & Refractive Eye Surgery Today, 2011, 49-40.*
Bagiyan et al, Russian Chemical Bulletin, International Edition, 2003, 52(5), 1135-1141.*
Abelson et al., 2008, Tear Substitutes. In: Albert and Miller, eds. Principles and Practices of Ophthalmology, 3rd edition, vol. 1. Philadelphia: W.B. Saunders Company, 287-292.
Akyol-Salman, Azizi et al., 2010, Efficacy of topical N-acetylcysteine in the treatment of meibomian gland dysfunction, J Ocul Pharmacol Ther (26): 329-333.
Behrens, Doyle et al., 2006, Dysfunctional tear syndrome: a Delphi approach to treatment recommendations, Cornea (25): 900-907.
Bernkop-Schnurch et al., Permeation enhancing polymers in oral delivery of hydrophilic macromolecules: Thiomer/GSH systems, J. Contr. Release 93(2003) 95-103.
Bernkop-Schnurch et al., 2004, Thiolated chitosans, Eur J Pharm Biopharm (57): 9-17.
Bernkop-Schnurch, 2005, Thiomers: a new generation of mucoadhesive polymers, Adv Drug Deliv Rev (57): 1569-1582.
Bonengel et al: "Thiomers—From bench to market", Journal of Controlled Release, Jun. 1, 2014, XP05514603.

(Continued)

*Primary Examiner* — Ganapathy Krishnan
(74) *Attorney, Agent, or Firm* — Workman Nydegger

(57) ABSTRACT

The present invention is concerned with a sterile aqueous ophthalmic solution comprising about 0.05% to about 0.5% (w/w) of N—(N-acetylcysteinyl-)chitosan or a pharmaceutically acceptable salt thereof in a carrier solution, wherein the N—(N-acetylcysteinyl-)chitosan has a content of free thiol groups in an amount of from 80 µmol/g polymer to 280 µmol/g polymer. The invention is also concerned with a container containing said ophthalmic solution as well as the use thereof in the prevention or treatment of dry eye syndrome or dry eye signs and/or symptoms.

17 Claims, 5 Drawing Sheets

(56) References Cited

OTHER PUBLICATIONS

Chang, Tsai et al., 1997, Heterogeneous N-deacetylation of chitin in alkaline solution, Carbohydr Res (303): 327-332.

Clausen et al., The Role of Glutathione in the Permeation Enhancing Effect of Thiolated Polymers, Pharm. Res. 19 (5) 2002, 602-608.

Dai, Tanaka et al., 2011, Chitosan preparations for wounds and burns: antimicrobial and wound-healing effects, Expert Rev Anti Infect Ther (9): 857-879.

Dangl et al., 2009, In vivo Evaluation of Ocular Residence Time of $^{124}$I-labelled Thiolated Chitosan in Rabbits Using MicroPET Technology, ARVO Meeting Abstracts (50): 3689.

Dutta, Dutta et al., 2004, Chitin and chitosan: Chemistry, properties and applications, J Sci Ind Res (63): 20-31.

Felt, Carrel et al., 2000, Chitosan as tear substitute: a wetting agent endowed with antimicrobial efficacy, J Ocul Pharmacol Ther (16): 261-270.

Garhöfer et al: "Chitosan-N-Acetylcysteine Eye Drops", Cataract & Refractive Surgery Today Europe, Nov. 1, 2011, pp. 49-50, XP055145970.

Geisberger, Gyenge et al., 2013, Chitosan-thioglycolic acid as a versatile antimicrobial agent, Biomacromolecules (14): 1010-1017.

Hongyok, Chae et al., 2009, Effect of chitosan-N-acetylcysteine conjugate in a mouse model of botulinum toxin B-induced dry eye, Arch Ophthalmol (127): 525-532.

Hornof et al., In Vitro Evaluation of the Permeation Enhancing Effect of Polycarbophil-Cystein Conjugates on the Cornea of Rabbits, J. Pharm. Sci. 91 (12) 2002, 2588-2592.

Hornof et al., Mucoadhesive ocular insert based on thiolated poly(acrylic acid): development and in vivo evaluation in humans; Journal of Controlled Release 89 (2003) 419-428.

Hornof, M., In vitro and in vivo evaluation of novel polymeric excipients in the ophthalmic field, Thesis, University of Vienna, 2003.

Hornof, Goyal et al., 2009, Thiolated Chitosan for the Treatment of Dry Eye—Evaluation in Mice Using the Controlled-Environment Chamber Model, ARVO Meeting Abstracts (50): 3663.

Kast and Bernkop-Schnurch, 2001, Thiolated polymers—thiomers: development and in vitro evaluation of chitosan-thioglycolic acid conjugates, Biomaterials (22): 2345-2352.

Lemp, 2008, Management of dry eye disease, Am J Manag Care (14): S88-101.

Schaumberg, Sullivan et al., 2003, Prevalence of dry eye syndrome among US women, Am J Ophthalmol (136): 318-326.

Schaumberg, Dana et al., 2009, Prevalence of dry eye disease among US men: estimates from the Physicians' Health Studies, Arch Ophthalmol (127): 763-768.

Schmitz et al: "Synthesis and characterization of a chitosan-N-acetyl cysteine conjugate", International Journal of Pharmaceutics, Elsevier BV, NL, vol. 347, No. 1-2, Nov. 29, 2007, pp. 79-85, XP022369799.

Wadhwa, Paliwal et al., 2009, Chitosan and its role in ocular therapeutics, Mini Rev Med Chem (9): 1639-1647.

Wang et al., Chitosan-NAC Nanoparticles as a Vehicle for Nasal Absorption Enhancement of Insulin, J. Biomed Mater Res Part B: Appl Biomater 88B: 150-161, 2009.

Yamashita et al., Synthesis and Evaluation of Thiol Polymers, J. Macromol.Sc. 26 (1989), 9, 1291-1304.

Zheng et al., Disulfide Cross-Linked Hyaluronan Hydrogels, Biomacromolecules 3 (6) 2002, 1304-1311.

Zhu, Su et al., 2012, Synthesis of thiolated chitosan and preparation nanoparticles with sodium alginate for ocular drug delivery, Mol Vis (18): 1973-1982.

International Preliminary Report on Patentability cited in PCT/EP2015/059674 dated Nov. 8, 2016.

\* cited by examiner

AQUEOUS OPHTHALMIC SOLUTION AND METHOD FOR TREATING DRY EYE SYNDROME

TECHNICAL FIELD

The present invention relates to an aqueous ophthalmic solution. The present invention also relates to a container containing the aqueous ophthalmic solution. The present invention further relates to a method of treating dry eye syndrome using the novel aqueous ophthalmic solution. The method is useful in relieving dry eye signs and/or symptoms. The method involves administering to a subject in need thereof an aqueous ophthalmic solution containing a thiolated chitosan.

BACKGROUND OF THE INVENTION

Dry eye syndrome (DES), also referred to as dry eye disease, is a highly prevalent ocular surface disease. Approximately 40 million Americans are affected with some type of dry eye, a significant portion of which that are age 50 years and older have moderate-to-severe dry eye (Schaumberg, Sullivan et al., 2003, Prevalence of dry eye syndrome among US women, Am J Ophthalmol (136): 318-326; Schaumberg, Dana et al., 2009, Prevalence of dry eye disease among US men: estimates from the Physicians' Health Studies, Arch Ophthalmol (127): 763-768).

Broadly, dry eye disease can be any syndrome associated with tear film instability and dysfunction (such as increased tear evaporation and/or reduced aqueous secretion). Among the indications that are referred to by the general term "dry eye disease" are: Keratoconjunctivitis sicca (KCS), age-related dry eye, Stevens-Johnson syndrome, Sjogren's syndrome, ocular cicatrical pemphigoid, corneal injury, ocular surface infection, Riley-Day syndrome, congenital alacrima, nutritional disorders or deficiencies (including vitamin deficiencies), pharmacologic side effects, glandular and tissue destruction, autoimmune and other immunodeficient disorders, and inability to blink in comatose patients. Also included are dry eye symptoms caused by environmental exposure to airborne particulates, smoke, smog, and excessively dry air; as well as contact lens intolerance and eye stress caused by computer work or computer gaming.

There are other diseases that have a high degree of co-morbidity with dry eye disease: Allergic conjunctivitis (seasonal and chronic), blepharitis and Meibomian gland dysfunction. These conditions affect the quality and stability of the tear film, which results in dry eye signs and symptoms.

Laser assisted vision correction procedures such as photorefractive keratectomy (PRK), laser-assisted sub-epithelial keratectomy (LASEK) and laser-assisted in situ keratomileusis (LASIK) also negatively influence tear film functionality and frequently cause (temporary) dry eye disease.

Currently the management of DES encompasses both pharmacologic and non-pharmacologic treatments, including environmental management, avoidance of exacerbating factors, lid hygiene, tear supplementation (artificial tears), secretagogues (to increase the production of tears), punctual plugs, anti-inflammatory agents (cyclosporine, steroids), moisture chamber, and even salivary gland auto transplantation (Behrens, Doyle et al., 2006, Dysfunctional tear syndrome: a Delphi approach to treatment recommendations, Cornea (25): 900-907). Currently available options for treating DES are inadequate. Even tear supplementation is not an ideal treatment option as it requires the subject to repeat artificial tear installation very many times during the day.

Various polymers have been disclosed as possible aids in providing some benefit to alleviating DES symptoms and in fact some artificial tears contain one or more polymers, including the currently top 5 best selling over-the-counter (OTC) products for dry eye within the EU (Celluvisc®, Systane®, Hylo-Comod®, Optive® and Artelac®). These polymers are intended to protect ocular mucous membranes and provide lubrication for the ocular surface. Examples include cellulose derivatives, hyaluronic acid, liquid polyols, polyvinyl alcohol, povidone, carbopol and hydroxypropyl-guar. Polymers used in products to treat DES have relatively short residence time on the ocular surface and require frequent instillation. In order to increase ocular residence time, some formulations contain petroleum jelly or mineral oil; however, due to significant blurring these highly viscous products can only be used in the evening prior to sleep. (Abelson et al., 2008, Tear Substitutes. In: Albert and Miller, eds. Principles and Practices of Ophthalmology, 3rd edition, vol. 1. Philadelphia: W.B. Saunders Company, 287-292). All other tear substitutes have to be instilled repeatedly during the day.

Some potential improvements to these polymers have been disclosed. One potential improvement could be to use a polymer that has significant mucoadhesive properties in order to increase residence time of the formulation on the ocular surface without causing significant blurring. Chitosan, a polycationic polymer which is derived from the natural polymer chitin, is well known for its mucoadhesive properties. Ocular residence time of ophthalmic formulations containing chitosan can be increased not only due to its viscosity enhancing properties but also because of interactions of chitosan with negatively charged mucins on the ocular surface (Wadhwa, Paliwal et al., 2009, Chitosan and its role in ocular therapeutics, Mini Rev Med Chem (9): 1639-1647). In addition, chitosan has antimicrobial activity against various pathogenic microorganisms (Felt, Carrel et al., 2000, Chitosan as tear substitute: a wetting agent endowed with antimicrobial efficacy, J Ocul Pharmacol Ther (16): 261-270; Dai, Tanaka et al., 2011, Chitosan preparations for wounds and burns: antimicrobial and wound-healing effects, Expert Rev Anti Infect Ther (9): 857-879).

Thiolation of polymers has been disclosed to further increase their mucoadhesive properties. EP 1126881 B1 discloses a mucoadhesive polymer comprising at least one non-terminal thiol group. The use of thiolated polysaccharides for preparing an implant for tissue augmentation is disclosed in WO 2008/077172, wherein said thiolated polymers are characterised by the formation of disulfide bonds which leads to a stabilisation of the polymeric network. The priority application of WO 2008/077172, A 2136/2006, discloses further application fields for thiolated polymers.

Modification of chitosan by covalent attachment of thiol group bearing ligands (i.e., thiolation) has been disclosed. It has also been disclosed that thiolation increases the mucoadhesive properties of chitosan (Kast and Bernkop-Schnurch, 2001, Thiolated polymers—thiomers: development and in vitro evaluation of chitosan-thioglycolic acid conjugates, Biomaterials (22): 2345-2352; Bernkop-Schnurch, Hornof et al., 2004, Thiolated chitosans, Eur J Pharm Biopharm (57): 9-17; Bernkop-Schnurch, 2005, Thiomers: a new generation of mucoadhesive polymers, Adv Drug Deliv Rev (57): 1569-1582; Schmitz, Grabovac et al., 2008, Synthesis and characterization of a chitosan-N-acetyl cysteine conjugate, Int J Pharm (347): 79-85). The antimicrobial efficacy of some thiolated chitosans was evaluated as well (WO2009132226 A1; WO2009132227 A1; WO2009132228 A1; Geisberger, Gyenge et al., 2013, Chitosan-thioglycolic acid as a versatile antimicrobial agent, Biomacromolecules (14): 1010-1017)

N-acetylcysteine (NAC) is a derivative of the thiol group bearing amino acid L-cysteine. NAC is a reducing agent with antioxidative activity. It is also well known for its ability to reduce mucus viscosity by reducing mucin disulfide bonds. Due to these mucolytic properties NAC is widely used to reduce mucus viscosity in broncho-pulmonary disorders with excessive mucus production. Topical ophthalmic formulations containing the mucolytic and antioxidant agent NAC are used for the treatment of corneal diseases such as meibomian gland dysfunction and DES (Lemp, 2008, Management of dry eye disease, Am J Manag Care (14): S88-101; Akyol-Salman, Azizi et al., 2010, Efficacy of topical N-acetylcysteine in the treatment of meibomian gland dysfunction, J Ocul Pharmacol Ther (26): 329-333). EP 0 551 848 B1 discloses an ophthalmic pharmaceutical composition for the treatment of DES containing NAC in a concentration between 3% and 5% (w/v) and polyvinylalcohol.

It has been disclosed that thiolation of chitosan using NAC increases its ocular residence time on rabbit eyes when compared with non-thiolated chitosan (Dangl, Hornof et al., 2009, In vivo Evaluation of Ocular Residence Time of $^{124}$I-labelled Thiolated Chitosan in Rabbits Using Micro-PET Technology, ARVO Meeting Abstracts (50): 3689).

It has been disclosed that N—(N-acetylcysteinyl-)chitosan HCl has some beneficial effect on the ocular surface of the mouse eye in mouse dry eye models (Hongyok, Chae et al., 2009, Effect of chitosan-N-acetylcysteine conjugate in a mouse model of botulinum toxin B-induced dry eye, Arch Ophthalmol (127): 525-532; Hornof, Goyal et al., 2009, Thiolated Chitosan for the Treatment of Dry Eye—Evaluation in Mice Using the Controlled-Environment Chamber Model, ARVO Meeting Abstracts (50): 3663).

Further publications reviewing and discussing various uses of thiolated polymers are listed below:

Hornof et al., Mucoadhesive ocular insert based on thiolated poly(acrylic acid): development and in vivo evaluation in humans; Journal of Controlled Release 89 (2003) 419-428; Hornof, M., In vitro and in vivo evaluation of novel polymeric excipients in the ophthalmic field, Thesis, University of Vienna, 2003; Bernkop-Schnurch et al., Permeation enhancing polymers in oral delivery of hydrophilic macromolecules: Thiomer/GSH systems, J. Contr. Release 93 (2003) 95-103; M. Hornof et al., In Vitro Evaluation of the Permeation Enhancing Effect of Polycarbophil-Cystein Conjugates on the Cornea of Rabbits, J. Pharm. Sci. 91 (12) 2002, 2588-2592; and Clausen et al., The Role of Glutathione in the Permeation Enhancing Effect of Thiolated Polymers, Pharm. Res. 19 (5) 2002, 602-608; Yamashita et al., Synthesis and Evaluation of Thiol Polymers, J. Macromol. Sc. 26 (1989), 9, 1291-1304; Zheng et al., Disulfide Cross-Linked Hyaluronan Hydrogels, Biomacromolecules 3 (6) 2002, 1304-1311; Wang et al., Chitosan-NAC Nanoparticles as a Vehicle for Nasal Absorption Enhancement of Insulin, J. Biomed Mater Res Part B: Appl Biomater 88B: 150-161, 2009; WO 2008/094675 A2; U.S. Pat. No. 5,412, 076 A.

However, so far no formulation containing thiolated chitosan has been disclosed which fulfills the requirements of long-term stability, tolerability, safety, effectiveness in the treatment of dry eye syndrome and improved patient compliance. As a result of the ineffectiveness and inconvenience of current therapies of dry eye treatment, there remains a need for a method of treating dry eye syndrome that fulfills the requirements listed above.

SUMMARY OF THE INVENTION

The present invention is directed to an aqueous ophthalmic solution containing a thiolated chitosan. More particularly, the present invention is directed to a sterile aqueous ophthalmic solution containing about 0.05% to about 0.5% (w/w) of N—(N-acetylcysteinyl-)chitosan or a pharmaceutically acceptable salt thereof, in a carrier solution, wherein the N—(N-acetylcysteinyl-)chitosan has a content of free thiol groups in an amount of about 80 µmol/g polymer to about 280 µmol/g polymer.

The present invention is, furthermore, directed to a container comprising said aqueous ophthalmic solution.

The present invention is also directed to the specific use of said aqueous ophthalmic solution in the prevention or treatment of dry eye syndrome dry eye signs and/or symptoms. Accordingly, the present invention is also directed to a method of treating said diseases and symptoms in a subject in need of such treatment. The method comprises the step of first identifying a subject suffering from dry eye syndrome or dry eye symptoms, then administering to the subject an effective amount of the aqueous ophthalmic solution containing N—(N-acetylcysteinyl-)chitosan or a pharmaceutically acceptable salt thereof.

Particularly, the present invention is suitable for treating dry eye signs and/or symptoms caused by or connected with one or more of keratoconjunctivitis sicca (KCS), age-related dry eye, Stevens-Johnson syndrome, Sjogren's syndrome, ocular cicatrical pemphigoid, corneal injury, infection, Riley-Day syndrome, congenital alacrima, PRK, LASEK and/or LASIK treatments, allergic conjunctivitis, blepharitis and meibomian gland dysfunction, nutritional disorders or deficiencies (including vitamin deficiency), pharmacologic side effects, glandular and tissue destruction, autoimmune and other immunodeficient disorders, and inability to blink in comatose patients. Also included are dry eye symptoms caused by environmental exposure to airborne particulates, smoke, smog, and excessively dry air; as well as contact lens intolerance and eye stress caused by computer work or computer gaming.

DETAILED DESCRIPTION OF THE INVENTION

Figure 1:
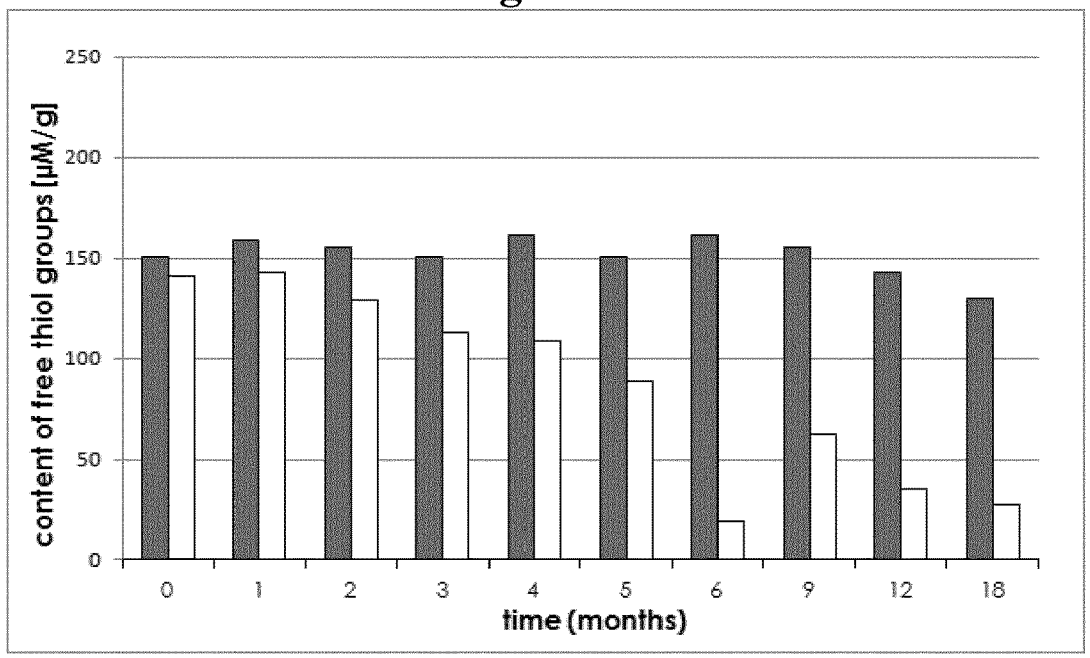
FIG. 1 shows a comparison of the stability of free thiol groups in an aqueous ophthalmic solution containing 0.1% (w/w) N—(N-acetylcysteinyl-)chitosan.HCl during long term storage at 25° C. and 40% relative humidity using different packaging as described in Example 3. Grey bars depict thiol group content at different time points (starting point, 1 month, 2 months, 3 months, 6 months, 9 months, and 12 months) during storage in group 1 (packaging and storage with oxygen absorber), white bars depict thiol group stability in group 2 (packaging and storage without oxygen absorber).

The inventors have unexpectedly discovered a stable ophthalmic solution that is effective in treating dry eye syndrome or improving one or more dry eye signs and/or symptoms in patients suffering from dry eye syndrome and/or improving the quality of the tear film in patients with dry eye disease. The present inventive sterile aqueous ophthalmic solution contains about 0.05% to about 0.5% (w/w) of N—(N-acetylcysteinyl-)chitosan or a pharmaceutically acceptable salt thereof, in a carrier solution, wherein the N—(N-acetylcysteinyl-)chitosan has a content of free thiol groups in an amount of about 80 µmol/g polymer to about 280 µmol/g polymer. Preferably, as the pharmaceutically acceptable salt the hydrochloride salt is employed.

In the following, the term "chitosan-NAC" stands for both N—(N-acetylcysteinyl-)chitosan and pharmaceutically acceptable salts thereof.

The method of the present invention is an improvement upon the current most commonly used treatment of dry eye disease—artificial tears (i.e., saline solution or solutions containing polymers) and anti-inflammatory agents (cyclosporine).

The present invention is suitable for treating any dry eye syndrome. Broadly, dry eye syndrome or dry eye disease as pertaining to the present invention can be any syndrome associated with tear film instability and/or dysfunction (such as increased tear evaporation and/or reduced aqueous secretion).

Particularly, the present invention is suitable for treating dry eye diseases caused by or connected with one or more of keratoconjunctivitis sicca, age-related dry eye, Stevens-Johnson syndrome, Sjogren's syndrome, ocular cicatrical pemphigoid, corneal injury, infection, Riley-Day syndrome, congenital alacrima, PRK, LASEK and/or LASIK treatments, allergic conjunctivitis, blepharitis and meibomian gland dysfunction, nutritional disorders or deficiencies (including vitamin deficiencies), pharmacologic side effects, glandular and tissue destruction, autoimmune disorders, immuno-deficient disorders, and inability to blink in comatose patients. Also included are dry eye symptoms caused by environmental exposure to airborne particulates, smoke, smog, and excessively dry air; as well as contact lens intolerance and eye stress caused by computer work or computer gaming.

As stated in the background, there are other diseases that have a high degree of co-morbidity with dry eye disease: Allergic conjunctivitis (seasonal and chronic), blepharitis and Meibomian gland dysfunction. These conditions affect the quality and stability of the tear film, which results in dry eye signs and symptoms.

Laser assisted vision correction procedures such as photorefractive keratectomy (PRK), laser-assisted sub-epithelial keratectomy (LASEK) and laser-assisted in situ keratomileusis (LASIK) also negatively influence tear film functionality and frequently cause (temporary) dry eye disease.

The present method of treatment comprises the steps of: (i) identifying a subject suffering from dry eye disease; and (ii) administering to the eyes of the subject an aqueous ophthalmic solution comprising an aqueous ophthalmic solution containing chitosan-NAC; wherein said dry eye disease is caused by or connected with one or more of the diseases, syndromes and stress factors mentioned above.

One significant advantage of the formulation of the present invention is that, following a single instillation onto the subject's eye, chitosan-NAC has a restorative effect on the tear film thickness for up to 24 h. This means that a subject does not have to constantly instill the product in the eye as would be needed for tear replacement therapy, such as when using artificial tears. The daily topical dose of the aqueous ophthalmic chitosan-NAC solution, effective to reduce dry eye symptoms and/or to improve tear film composition can be divided among one or several unit dose administrations. A subject would use the product as needed, but generally this would not be more than twice a day and in many instances the product would be used only once a day. A preferred regimen for the chitosan-NAC solution of the present invention is one drop of 0.1% (w/w) solution per eye once a day. Thus, a significant advantage of the formulation of the present invention is that it could be a once a day product and would ensure better patient compliance.

After treatment by the present methods, one or more dry eye signs and/or symptoms are reduced or alleviated in the subject. Dry eye symptoms include dryness, burning, ocular itching, ocular discomfort, photophobia, foreign body sensation, blurry vision, grittiness, and visual disturbance and/or loss, including blurred vision, reduced reading speed, photophobia, and loss in visual acuity. Dry eye signs are assessed by measurements such as: corneal and/or conjunctival staining (using fluorescein, lissamine green or rose Bengal stain), Schirmer's strip testing, Zone-Quick threads, tear film osmolarity, tear break-up-time and tear meniscus height.

One reason the signs and/or symptoms of DES are improved using the formulation of the present invention is possibly the restorative effect of the formulation on the ocular tear film thickness, which may be caused by a chemical interaction of the thiolated chitosan with ocular surface mucins or the presence of a protective coating on the ocular surface which is formed by crosslinking of chitosan-NAC after application to the ocular surface, or a combination of both effects.

The "effective amount" of the aqueous ophthalmic solution containing the chitosan-NAC polymer administered to a subject is an amount effective to reduce the clinical signs and/or symptoms of dry eye disease. This amount comprises about 0.05% to about 0.5% (w/w) of chitosan-NAC polymer, in a carrier solution.

At an amount below 0.05% the chitosan-NAC is in such a low concentration that no clinical effect would be seen in a patient. At much over 0.5% the patient tolerance starts to suffer and any permeation enhancing effects of chitosan are more pronounced. The concentration of the chitosan-NAC in the aqueous ophthalmic solution is preferably 0.05 to 0.3% (w/w), more preferably 0.05 to 0.2% (w/w), most preferred 0.08-0.16% (w/w). At a concentration much below 0.05% the mucoadhesive properties and consequently the clinical effect are not as pronounced. At a concentration much over 0.3% the high viscosity of the chitosan-NAC formulation leads to the formation of "clumps" after ocular application and the solution is not as evenly spread out on the ocular surface. Solutions of chitosan-NAC in a concentration range of 0.05% to 0.3% are evenly distributed on the ocular surface as demonstrated by in vivo studies with Iodine-$^{124}$ radiolabeled chitosan-NAC (see examples 9 and 10). The concentration of chitosan-NAC in the aqueous ophthalmic solution is most preferably about 0.1% as both clinical effect and patient tolerance are optimal.

A large percentage of the thiol groups bound on the chitosan-NAC that are present in the aqueous ophthalmic solution needs to be in the form of free thiol groups, that is to say, non-crosslinked thiols as defined below. It is important that the majority of these thiol groups remain free so as to only react upon installation onto the ocular surface. In some instances the amount of free thiol groups could be fairly low and still provide some pharmaceutical benefit to the eye when it is instilled. However, it is preferable that the chitosan-NAC polymer in the formulation of the present invention has a content of free thiol groups in an amount from about 80 µmol/g polymer to 280 µmol/g polymer; preferably with a range of free thiol groups of about 105 µmol/g polymer to 250 µmol/g polymer, more preferably of from 110 µmol/g polymer to 250 µmol/g polymer and most preferably of from preferably 140 to 250 µmol/g polymer.

At a free thiol group concentration much below 80 µmol/g polymer interactions between chitosan-NAC and mucins are weak and comparable to unmodified chitosan HCl, however at very high concentrations of free thiol groups of 300 µmol/g and more, the physicochemical properties of the core polymer chitosan are changed to such an extent that the polymer is not useful for preparation of an aqueous ophthalmic solution due to its reduced cationic character and limited solubility in water.

This amount of free thiol groups immobilised on the chitosan-NAC needs to be present when the ophthalmic formulation of the present invention is ready to be used in the eyes of the dry eye patient. This means that the free thiol groups present in the aqueous ophthalmic solution of the present invention must survive relatively long storage times. Therefore, the resulting dry eye product must be stable and retain the above stated free thiol groups for at least about 12 months, more preferably at least about 18 months, and even more preferably at least about 24 months.

The amount of free thiol groups immobilised on chitosan-NAC in an aqueous ophthalmic solution can be determined by the skilled artisan in a known way, such as via Ellman's reagent (see example 1).

In addition to the fact that a high amount of free thiol groups on the chitosan-NAC polymer in the aqueous ophthalmic solution is important, a low amount of crosslinked thiols (disulfides) on the chitosan-NAC polymer in the solution of the present invention is also preferable. During preparation and storage of the aqueous ophthalmic solution crosslinking of thiol groups immobilised on the chitosan-NAC can occur. A low amount of crosslinked thiols present in the formulation is a preferred parameter of the chitosan-NAC polymer formulation of the present invention.

Therefore, according to a preferred embodiment of the present invention, the amount of crosslinked thiol groups in the N—(N-acetylcysteinyl-)chitosan is 30% or less of the total thiol groups therein, preferably 25% or less, most preferably 15% or less.

Especially, in this preferred embodiment, the amount of crosslinked thiol groups in the N—(N-acetylcysteinyl-)chitosan is 30% or less of the total thiol groups therein, preferably 25% or less, most preferably 20% or less after storage of the solution for at least 12 months at room temperature.

If the amount of crosslinked thiol groups present in the formula was too high, the properties of the aqueous ophthalmic solution could change outside of the desired parameters, for example, the viscosity of the aqueous ophthalmic solution could become too high to be suitable for eye drops.

As explained below in more detail, it has been found that it is possible to produce a chitosan-NAC the thiol groups of which are not or only minimally crosslinked, such as with an amount of crosslinked thiol groups of less than 5%, preferably 4% or less of the total thiol groups. Especially if such a chitosan-NAC is employed for the manufacture of the ophthalmic solution of the present invention, the free thiol groups tend to be stable during the entire life cycle of the solution:

Thus, it has been found that upon employing such a chitosan-NAC during production of the formulation the increase of crosslinked thiol groups is <10% of the amount of free thiol groups initially present on the chitosan-NAC raw material. Furthermore, during storage of the solution over 12 months or even 18 months the increase of crosslinked thiol groups is <15% of the amount of free thiol groups initially present in the formulation. Finally, even if a second container of the solution (as defined below) which provides an oxygen barrier is opened, 30 days after opening the increase of crosslinked thiol groups is <15% of the amount of free thiol groups initially present in the formulation before opening.

Essentially the thiolated chitosan ophthalmic formulation of the present invention is made according to the following steps:

1. Chitin is isolated from crustaceous shells, such as shrimp or snow crab shells,
2. Chitosan is prepared from chitin through a chemical process that is well known in the art as, for example alkaline deacetylation;
3. The chitosan is thiolated by the covalent attachment of a thiol bearing ligand, such as with the use of N-acetylcysteine as is set forth herein;
4. The chitosan-NAC is then formulated in the form of an aqueous ophthalmic solution as is set forth herein; and
5. The aqueous ophthalmic solution containing chitosan-NAC is then put into a suitable container that would ensure its stability as is set forth herein.

As described in detail herein, chemically, chitosan is a polycationic biopolymer with favourable biological properties such as high biocompatibility and low toxicity. The source of the raw materials to produce the chitosan for the formulation of the present invention is not critical as long as the resulting chitosan is fairly pure and free from contaminants. For example, chitosan can also be produced from a non-animal source. The chitosan of the present invention can be processed by various methods so long as the chitosan has the properties required and set forth in the present specification. Most commonly, the raw material for the chitosan comes from chitin in the shells of crustaceans. Chitin can be obtained during the harvesting of crustaceous food sources such as lobster, crab, and shrimp. One preferred raw material source of chitin for the chitosan processed and used in the formulation according to the present invention is from the snow crab (Chionoecetes opilio) shells. Various sources of crustaceans could be used in obtaining the chitin to make the chitosan as long as the supply would be adequate. The preparation of chitosan from raw material biological sources is well known and disclosed in numerous scientific publications, for example (Chang, Tsai et al., 1997, Heterogeneous N-deacetylation of chitin in alkaline solution, Carbohydr Res (303): 327-332; Dutta, Dutta et al., 2004, Chitin and chitosan: Chemistry, properties and applications, J Sci Ind Res (63): 20-31).

The chitosan-NAC can be synthesized by reacting the chitosan with a thiol-group bearing ligand. Methods for thiolation are disclosed in numerous scientific publications, for example (Seki, Aoi et al., 1999, Partially deacetylated chitin or chitosan derivative with selectively substituted free amino group by amino acid and peptide and having substantially no substituted hydroxide group, and its manufacture, JP2000-302803; Bernkop-Schnurch, Hornof et al., 2004, Thiolated chitosans, Eur J Pharm Biopharm (57): 9-17; Schmitz, Grabovac et al., 2008, Synthesis and characterization of a chitosan-N-acetyl cysteine conjugate, Int J Pharm (347): 79-85; Zhu, Su et al., 2012, Synthesis of thiolated chitosan and preparation nanoparticles with sodium alginate for ocular drug delivery, Mol Vis (18): 1973-1982).

The chitosan-NAC used in the present invention needs to be water soluble in the concentration range useful for the preparation of the aqueous ophthalmic solution and the resulting solutions need to be clear and colorless. Salt formation of chitosan-NAC with organic or anorganic acids increases the aqueous solubility of chitosan. Suitable salts of thiolated chitosan of the present invention include any pharmaceutically acceptable salts with organic acids such as acetic, citric, formic and tartaric acid, as well as mineral acids such as HCl and $H_2SO_4$. The chitosan-NAC hydrochloride salt is a preferred embodiment of the present invention.

What is important is that such reaction pathways and reaction conditions are used that after synthesis and purification essentially all thiol groups immobilised on the chitosan backbone are present in the free form and not in the crosslinked form as disulfides, i.e. are only minimally crosslinked. Virtually all attached thiols in the thiolated chitosan of the present invention are in the form of free thiol groups, i.e. they are not cross-linked. A minimal amount of crosslinking during synthesis is only acceptable as long as the viscosity of the thiolated chitosan remains within the stated parameters and its aqueous solubility is sufficient for the preparation of an aqueous ophthalmic solution.

It has been found that it is possible to manufacture chitosan-NAC with a very low or even zero degree of crosslinking of the thiol groups by exposing the chitosan-NAC to a reducing agent after its synthesis, for example after alkaline hydrolysis of the thioacetyl moieties. The reducing agent may be selected from the group of DTT, TCEP or $NaBH_4$, $NaBH_4$ being preferred. It has, furthermore, been found that the reduction step should be carried out at elevated temperature, such as 30° C. or more or preferably 40° C. or more. Furthermore, high amounts of reducing agents need to be employed, such as with a stoichiometric ratio of reducing agent to the chitosan backbone polymer of 2:1 or more.

Chitosan-NAC polymers with a degree of crosslinked thiol groups of less than 5%, preferably 4% or less of the total thiol groups can be synthesized according to this embodiment.

The viscosity in aqueous solution of the final chitosan-NAC of the present invention preferably falls within a certain range, and the present inventors have unexpectedly discovered that the viscosity of the chitosan-NAC only falls within this preferred range if during the production of the chitosan-NAC the chitosan-NAC is processed under certain conditions and within certain parameters, particularly according to the reduction conditions stated above, which lead to polymers which are only minimally crosslinked. The viscosity of the resulting product preferably falls within an acceptable range so that the chitosan-NAC will be most useful in the resulting eye drop formulation. Thus, the kinematic viscosity (0.5% in water at 25° C.) of the chitosan-NAC polymer is preferably within the range of about 1 to 15 $mm^2/s$, more preferably within the range of about 2 to 10 $mm^2/s$. If the viscosity is too high, then a useful eye drop solution cannot be made with the preferred concentration range of chitosan-NAC in the formulation, as the polymer will remain as an insoluble viscous mass in the container.

The chitosan-NAC needs to be purified to be useful in the formulation of the present invention (such as after step #3 above and, especially, after treatment of the chitosan-NAC with the reducing agent). The chitosan-NAC should be washed in such a way that the resulting product is pure. One known method is disclosed in Kast and Bernkop-Schnurch, 2001, Thiolated polymers—thiomers: development and in vitro evaluation of chitosan-thioglycolic acid conjugates, Biomaterials (22): 2345-2352.

Another method would be washing the chitosan-NAC with polar solvents followed by drying in order to remove the solvents. One preferred solvent is isopropyl alcohol, since it is non-toxic, readily available, and economical, however other solvents, and other alcohols other than isopropyl alcohol could work as well. This washing can be repeated as needed, depending upon the volume of solvent used each time. Preferably the washing and drying step is repeated at least one time.

The drying step can be conducted at room temperature and at standard humidity, but this process can be very time consuming. Therefore, the drying process is preferably conducted at an elevated temperature and/or under reduced pressure. The drying of the chitosan-NAC is preferably conducted at an elevated temperature of at least about 40° C. to about 70° C. and preferably for at least about five hours. A more preferred drying process is conducted at temperatures of at least about 50° C. to about 60° C. for about 10 to 24 hours. One preferred multi-step purification process would be to wash the chitosan-NAC polymer three times with isopropyl alcohol and to recover the solid by centrifugation followed by drying at about 60° C. for about 15 to 20 hours.

The aqueous ophthalmic solution according to the present invention can contain at least one ophthalmic compatible excipient. Any excipient suitable for example to adjust the tonicity, the viscosity of the solution or to stabilise the pH, to increase the solubility of the active ingredient, to increase ocular comfort after application, or to stabilise the formulation in general, can be employed.

The pH of the aqueous ophthalmic solution is adjusted by adding any physiologically and ophthalmic acceptable pH adjusting acids, bases, or buffers to have a pH within the range of about 5.5 to about 7. A pH much below about 5.5 would be outside of the physiological acceptable parameters (the solution would cause a severe stinging or burning sensation in the eye). At a pH much above 7, forming a stable solution of the chitosan-NAC where it does not precipitate out of solution is difficult. Thus, due to the ease of formulating a stable solution, a pH below 7 is preferred. The preferred pH of the aqueous ophthalmic solution of the present invention is between about 5.8 to about 6.8, with a pH of 6.0 to 6.6 being most preferred.

Examples of suitable acids used in the formulation of the present invention include acetic, boric, citric, lactic, phosphoric, hydrochloric, and the like, and examples of bases include sodium hydroxide, sodium phosphate, sodium borate, sodium citrate, sodium acetate, sodium lactate, tromethamine, THAM (trishydroxymethylamino-methane), and the like. A preferred embodiment of the present invention is a boric acid and sodium borate buffer system, which also contains a polyol such as mannitol to increase buffer capacity at the most preferred pH range of 6.0 to 6.6.

Examples of suitable excipients used in the formulation of the present invention to increase stability of the formulation include disodium ethylenediaminetetraacetate ($Na_2$-EDTA), sodium metabisulfite, mannitol, polyethylene glycol and the like.

The osmolarity of the topical ophthalmic formulation of the present invention is generally from about 150 to about 400 milliosmolar (mOsM), more preferably from about 200 to about 350 mOsM, with the osmolarity of about 250 to about 330 mOsM being most preferred. The osmolarity can be adjusted by using appropriate amounts of physiologically and ophthalmic acceptable ionic or non-ionic agents. Sodium chloride is a common osmotic agent. Equivalent amounts of one or more salts made up of cations such as potassium, ammonium and the like and anions such as chloride, citrate, ascorbate, borate, phosphate, bicarbonate, sulfate, thiosulfate, bisulfate, and the like can be used in addition to or instead of sodium chloride to achieve osmorality within the above-stated range. Further, non-ionic agents such as mannitol, dextrose, sorbitol, glycerol, glucose and the like can also be used to adjust the osmolarity. Sodium chloride and mannitol are the preferred agents to adjust osmotic pressure.

The ophthalmic formulation can contain lubricants to provide a high ocular comfort level suitable for the regular application necessary in the treatment of DES. There are many types of lubricating agents such as polyvinylpyrrolidone, polyvinylalcohol, liquid polyols, hyaluronic acid and pharmaceutically acceptable salts thereof, lubricin and cellulose derivatives; however preferred agents are polyethylene glycol and hydroxypropyl methylcellulose (HPMC).

In a preferred embodiment, the ophthalmic solution according to the present invention contains the following excipients in addition to N—(N-acetylcysteinyl-)chitosan hydrochloride:

Boric acid in an amount from 1.0 to 16.0 mg/ml, preferably 8 to 16 mg/ml;
Polyethylenglycol 400 in an amount from 0.01 to 5.0 mg/ml, preferably 1 to 5 mg/ml;
$Na_2$-EDTA in an amount from 0.01 to 0.5 mg/ml;
Mannitol in an amount from 0.01 to 5.5 mg/ml, preferably 0.1 to 4 mg/ml;
Sodium chloride in an amount from 0.01 to 9 mg/ml, preferably 1 to 3 mg/ml; and
Hydroxypropyl methylcellulose in an amount from 0.01 to 20 mg/ml, preferably 1 to 3 mg/ml.

The ophthalmic solution according to the present invention has to be sterile and can be sterilized in any suitable manner. One particular preferred sterilization method is sterile filtration. The ophthalmic solution according to the present invention can contain preservatives, such as benzalkonium chloride, although this is less preferred.

The aqueous ophthalmic solution containing chitosan-NAC can be administered to the eyes of a patient by any suitable means for topical administration. This is preferably in the form of an aqueous eye drop solution. This solution can be in a single use container that is sterile until opened and thus does not need to have a preservative, or it can be in the form of a multi-use container that remains sterile after opening or in a multi-use container with a formulation containing a preservative.

The thiol groups of chitosan-NAC polymers tend to form disulfide bonds in aqueous solutions, thus reducing the mucoadhesive properties of chitosan-NAC. It was discovered that this tendency depends on the presence of oxygen in the aqueous ophthalmic solution.

It has been found that it is possible to stabilize the free thiol groups of the chitosan-NAC employed according to the present invention in aqueous solution even more when storing the solution under oxygen-free conditions, or essentially oxygen-free conditions. The oxygen-free atmosphere can be a nitrogen atmosphere, vacuum atmosphere, or an atmosphere consisting of noble gases.

Thus, when the solution is put into a container it should be done so in the absence of oxygen. Further, after the container is filled with the aqueous ophthalmic solution of the present invention, it should remain oxygen free. Therefore, the present invention also relates to a container that keeps the aqueous ophthalmic solution free from oxygen during storage. Accordingly, one aspect of the present invention comprises an essentially oxygen free container containing the aqueous ophthalmic solution. As "essentially oxygen free", an atmosphere with an amount of 1.5% oxygen or less is to be understood. The concentration of dissolved oxygen in solution during production of the formulation and filling into the containers is below 1.0 mg/L, more preferably below 0.5 mg/L, even more preferably in the range of 0.1 mg/L.

In a preferred embodiment, the container is made of a material that is impervious to oxygen such that after filling, the ophthalmic solution remains essentially oxygen free for an extended period of time. Such containers could be glass or glass lined polymers, metal or metal lined polymers. In another preferred embodiment, the container is made of a polymer that has contained therein an oxygen absorber that would prevent oxygen from entering the solution through the walls of the container. Such oxygen absorbers include iron salts, sulfites, ascorbic acid, unsaturated fatty acid salts, metal-polyamide complexes or palladium/$H_2$ based systems. For example, WO 09/32526 discloses a film having an active oxygen barrier layer comprising an oxygen scavenging composition blended of a thermoplastic resin having carbon-carbon double bonds substantially in its main chain, a transition metal salt, and an oxygen barrier polymer with oxygen barrier properties.

Further, the container itself can be manufactured from a gas tight material with an oxygen scavenger embedded and an airless closure system.

In a preferred embodiment, there is provided a first container containing the ophthalmic solution and a second container containing said first container.

Thus, for example, the container that holds the ophthalmic solution of the present invention is itself contained inside of a gas tight sachet or pouch. In particular a sachet or pouch made of aluminium or an aluminium laminate or aluminium composition may contain therein one or more sub-containers (i.e. "first containers") containing the ophthalmic solution according to the invention. The second container, i.e. the sachet or pouch can also contain an additional oxygen absorber (for example PKT KH-20 Pharmakeep® or Stabilox® Oxygen Scavenger) as is used in some standard packaging. Even in the case where the sachet is sealed under vacuum or in an inert atmosphere, the addition of an oxygen absorber can be required in order to remove residual oxygen from the sub-container. The sachet can contain either one or more single dose containers or multi-dose containers, for example five single dose containers per sachet. In the case of the multi-dose container, it must preserve the ophthalmic solution according to the present invention in a sterile condition and in an essentially oxygen free condition.

The chitosan-NAC contained in the container according to the invention preferably has a content of free thiol groups of from 80 µmol/g polymer to 250 µmol/g polymer, preferably 105 µmol/g polymer to 250 µmol/g polymer after storage of at least 12 months at room temperature. This means that, according to the present invention, the free thiol groups remain on the chitosan-NAC and that the resulting formulation is stabile over an extended period of time. This period of time is preferably at least about 12 months, more preferably at least 18 months, and even more preferably at least about 24 months. This long stability preference is due to the fact that some products end up having long storage times and delays in commercial delivery and supply chains that could result in a less stable product falling out of acceptable parameters.

Furthermore, preferably the amount of crosslinked thiol groups in the chitosan-NAC contained in the container according to the invention is 30% or less of the total thiol groups therein, preferably 25% or less, most preferred 20% or less after being stored for at least 12 months, more preferably at least 18 months. As mentioned above, the stability of the free thiol groups in the solution is especially good if a chitosan-NAC with only a minimal degree of crosslinked thiol groups is employed for manufacturing the solution.

In the above-described embodiment where there is a second container, e.g. a gas tight sachet, containing one or more first container(s), e.g. single use containers made from LDPE, the content of free thiol groups in the solution preferably remains within the range as defined per the present invention after opening of the first container for at least 30 days. The therapeutic time needed for e.g. 5 containers is 5 days, thus this duration of stability is more than sufficient.

As mentioned above, it was found that especially if a chitosan-NAC with only a minimal degree of crosslinked thiol groups is employed for manufacturing the ophthalmic solution of the present invention, the free thiol groups remained stable even after the second container which provides the oxygen barrier was opened, i.e. it was found that 30 days after opening of the second container the increase of crosslinked thiol groups was <15% of the amount of thiol groups initially present in the solution before opening.

The present invention is concerned primarily with the treatment of human subjects, but can also be employed for the treatment of other mammalian subjects, such as dogs and cats, for veterinary purposes.

The invention is illustrated further by the following examples, which are not to be construed as limiting the invention to the specific procedures described therein.

EXAMPLES

Example 1: Determination of Thiol Group Content

Quantification of thiol groups is based on a wet chemistry method employing 5,5'-Dithio-bis(2-nitrobenzoic acid, DTNB, "Ellman's reagent"). Free thiol groups react with the reagent under formation of a mixed disulfide, whereas one equivalent of 2-Nitro-5-thiobenzoic acid is set free. In buffered alkaline medium (pH=8.05), the resulting thiolate gives a distinctly yellow coloured solution, whose absorption can be measured photometrically at 450 nm.

119.0-121.0 mg of the sample solution containing 0.1% N—(N-acetylcysteinyl-)chitosan hydrochloride were weighed in 1.5 ml Eppendorf vessels. Three values were determined from each solution. 25.0 mg N-acetylcysteine was accurately weighted and solved in 25.0 ml of borate buffer (pH 6.75). This solution was then further diluted for a calibration curve. Borate puffer was used for the blank value. To each solution phosphate buffer pH 8.0 was added to a final volume of 600 µl. 600 µl freshly prepared Ellman's solution (containing 20 mg of 5,5'-Dithio-bis(2-Nitrobenzoic acid) in 100 ml of phosphate buffer (pH 8.0)) was added to each solution (standard solution, sample solution and blank value). The solutions were well-mixed and incubated for 1.5 h under UV protection. Afterwards the sample solutions containing N—(N-acetylcysteinyl-)chitosan hydrochloride were centrifuged at 13400 rpm 5 minutes. Finally 1.1 ml of each solution (standard solution, sample solution and blank value) was transferred into a semimicrocuvettes and tested at 450 nm in a spectrophotometer against the blank value.

The mean content of free thiol groups of the thiolated chitosan in the sample solutions was determined to be 2.61% (w/v) which corresponds to a value of 178.5 µM free thiol groups/g polymer.

Example 2: Composition of the Formulation

The following aqueous ophthalmic solution was prepared using N—(N-acetylcysteinyl-)chitosan hydrochloride with a content of free thiol groups of 158 µM/g polymer and a kinematic viscosity (25° C., 0.5% aqueous solution) of 5.63 mm$^2$/s. All other ingredients are pharmaceutical additives. The solution was sterilized via sterile filtration.

The eye drop formulation had the following composition:

TABLE 1

| Composition of the aqueous ophthalmic solution | |
|---|---|
| Compound | Amount [mg] |
| N-(N-acetylcysteinyl-)chitosan hydrochloride | 1.0 |
| Boric acid | 12.4 |
| Polyethylenglycol 400 (PEG 400) | 3.0 |
| Na$_2$-EDTA | 0.42 |
| Mannitol | 2.0 |
| NaCl | 2.0 |
| HPMC | 1.5 |
| NaOH | q.s. |
| Aqua bidestillata | q.s. ad 1 ml |

The physical-chemical properties of the formulation were within the following specifications:

TABLE 2

| Physical-chemical properties of the aqueous ophthalmic solution | |
|---|---|
| pH-value | 6.0-6.6 |
| Osmolality [mOsmol/kg] | 250-330 |
| Content of free thiol groups [µMol/g polymer] | 140-250 |
| Content of thiolated chitosan [mg/ml] | 0.90-1.10 |
| Sterility | sterile |

This example shows that chitosan-NAC may be formulated according to the present invention to fulfil the requirements for ophthalmic preparations.

Example 3: Long Term Stability of the Aqueous Ophthalmic Solution

Group 1: A formulation according to the present invention containing 1 mg N—(N-acetylcysteinyl-)chitosan hydrochloride/ml was prepared under inert conditions and subsequently filled aseptically using blow-fill-seal technology into cards of five single dose containers made of LDPE (low density polyethylene) to a volume of 0.3 ml. Each card was packaged in an aluminium sachet containing an oxygen absorber (PKT KH-20 Pharmakeep®).

Group 2: A formulation according to the present invention containing 1 mg N—(N-acetylcysteinyl-)chitosan hydrochloride/ml was prepared, filled in cards of five single dose containers and packaged in aluminium sachets as described above, but in this group the aluminium sachets did not contain oxygen absorbers.

Samples of formulations prepared under manufacturing conditions for group 1 and group 2 were stored under controlled conditions at a temperature of 25° C. and 40% relative humidity for 18 months. The content of free thiol groups was measured as described in example 1 in regular time intervals. At the same time the concentration of oxygen inside the pouch was measured with an oxygen gas analyzer (PBI Dansensor CheckPoint II). The results of the thiol group measurements are shown in FIG. 1 (group 1: grey bars, group 2: white bars). The results indicate that when the aqueous ophthalmic formulation of the present invention containing chitosan-NAC polymer is stored in an essentially oxygen free atmosphere with maximum oxygen levels of less than 1.5% (as provided by an oxygen absorber) the free thiol content remains high, within acceptable parameters for a time period of at least 18 months. Surprisingly, even when stored without an oxygen absorber the thiol group content of the solution remained stable for a time period of about 1 month. After 4 months the thiol group content still remained within acceptable parameters but a decrease of thiol group content of 20% was observed. Oxygen levels in the pouches of group 2 were in the range of 3.0 to 5.7% during the entire storage period of 18 months.

Example 4: Short Term Stability of the Aqueous Ophthalmic Solution after Removal of Single Dose Containers from Aluminium Pouch A formulation according to the present invention containing 1 mg N—(N-acetylcysteinyl-)chitosan hydrochloride/ml was prepared under inert conditions and subsequently filled aseptically into cards of five single dose containers made of LDPE (low density polyethylene) to a volume of 0.3 ml using blow-fill-seal technology. Each card was packaged in an aluminium sachet containing an oxygen absorber (PKT KH-20 Pharmakeep®). Within one month after production the cards were removed from the pouches and stored in closed folding boxes under ambient air, humidity and temperature conditions for 30 days. The content of free thiol groups in the formulation was measured on day 0, day 5, day 12, day 19 and day 30.

Figure 2:
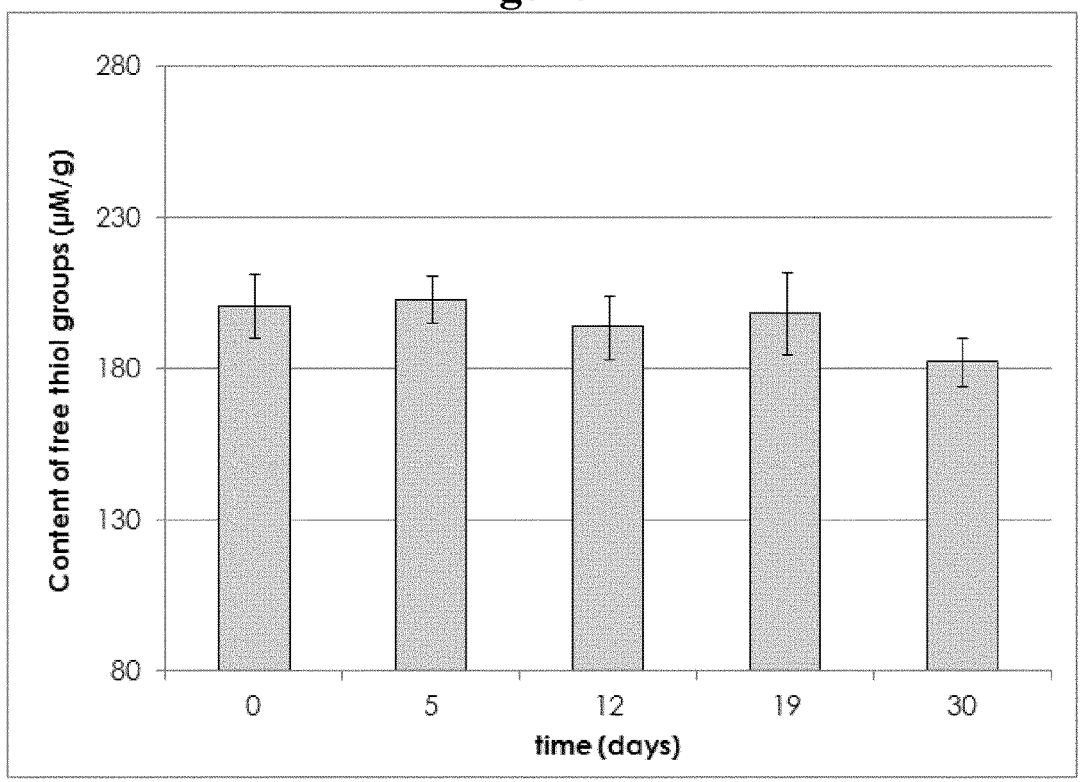
FIG. 2 shows the stability of free thiol groups in an aqueous ophthalmic solution containing 0.1% (w/w) N—(N-acetylcysteinyl-)chitosan.HCl during short term storage of single dose units under ambient air, humidity and temperature conditions for 30 days as described in Example 4.

The results are shown in FIG. 2 (mean values of 3 batches with standard deviations). These results indicate that the product remains within the desired parameters for a time period of 30 days when stored in LDPE single dose units in the presence of oxygen under ambient air conditions. The decrease of free thiol groups after 30 days was about 10%. Similar results were observed even when the aluminium sachet containing the cards were stored for 5 months at a temperature of 40° C. before removing the cards.

Example 5: Synthesis of N—(N-Acetylcysteinyl-)Chitosan Hydrochloride

Figure 3:
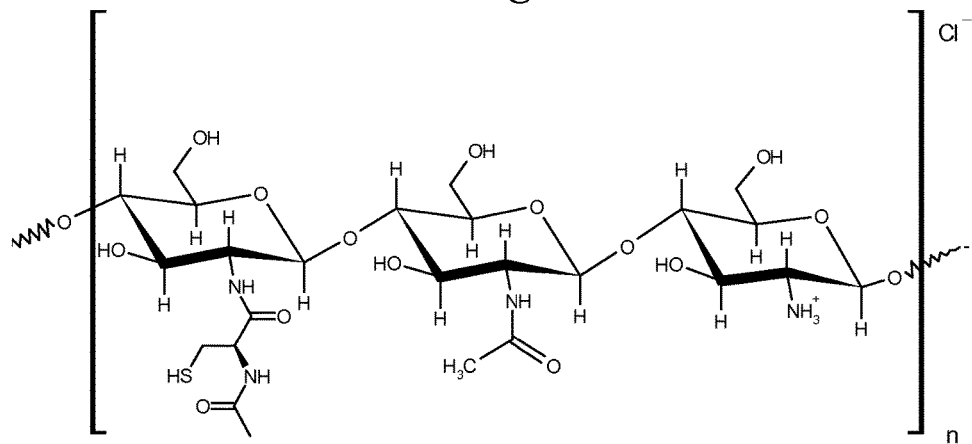
FIG. 3 shows a schematic drawing of a N—(N-acetylcysteinyl-)chitosan.HCl substructure.

N—(N-acetylcysteinyl-)chitosan hydrochloride polymers (FIG. 3) with different degrees of thiolation were synthesized by covalent attachment of N,S-diacetylcysteine to the primary amines of chitosan via nucleophilic substitution followed by release of free thiol groups in alkaline media. Different chitosans were used as raw materials for the synthesis (see Table 3). Data on the source and degree of deacetylation were provided by the supplier. Molecular weight was determined via size exclusion chromatography (SEC)-coupled triple detection using the Viscotek TDA305 from Malvern Instruments. The samples were dissolved in acetic acid 5% and separated isocratically on ViscoGEL columns.

TABLE 3

| List of chitosan raw material specifications | | | |
|---|---|---|---|
| Raw material (supplier) | Source | Degree of deacetylation | Molecular weight |
| Chitosan (Messrs. Primex) | *Pandalus borealis* | 85-95% | 25 kDa-250 kDa |
| Chitosan (Messrs. HMC+) | *Chionoecetes opilio* | 89%-93% | 100 kDa-250 kDa |
| Chitosan HCl (Messrs. HMC) | *Chionoecetes opilio* | 88% | 20 kDa |
| Chitosan HCl (Messrs. Aoxing) | Unspecified animal source | 91% | 150 kDa |

The resulting degree of thiolation was dependent on the weight ratio of chitosan and the active ester of N'S-diacetylcysteine as well as on the reaction conditions (pH value and temperature during nucleophilic substitution). Chitosan-NAC polymers with a degree of thiolization in the range of 40 µM/g polymer to 400 µM/g polymer were synthesized.

For the synthesis of the 5 different batches of chitosan-NAC polymer listed in Table 4 the following reaction conditions were employed: Chitosan with a molecular weight of 100 kDa to 250 kDa (supplier HMC+) was used as starting material. The weight ratio between chitosan and the active ester of N'S-diacetylcysteine was 1:1 (wt %) and the weight ratio between chitosan and the reducing agent sodium borohydride was 1:2 (wt %). The reduction with sodium borohydride was carried out at an elevated temperature of about 40° C.

TABLE 4

| Characterisation of chitosan-NAC polymers in terms of molecular weight and degree of thiolization | |
|---|---|
| Molecular weight | Degree of thiolization |
| 145 kDa | 220 µM/g polymer |
| 165 kDa | 225 µM/g polymer |
| 200 kDa | 210 µM/g polymer |
| 235 kDa | 220 µM/g polymer |
| 200 kDa | 220 µM/g polymer |

All chitosan-NAC polymers listed in Table 4 were suitable for the preparation of an aqueous ophthalmic solution according to the present invention in terms of water solubility, viscosity and thiol group content.

Example 6: Reaction Conditions for the Synthesis of Minimally Crosslinked Chitosan-NAC The covalent attachment of N,S-diacetylcysteine to the primary amines of chitosan was followed by alkaline hydrolysis of the thioacetyl-moities at pH 8±0.2. Resulting intra- and intermolecular disulfide bonds were then reduced under inert conditions at 40° C. using a large excess of sodium borohydride (chitosan:sodium borohydride=1:2 (wt.-%)). Subsequently, excess of sodium borohydride was destroyed by addition of 5N HCl which simultaneously generated the chitosan-NAC hydrochloride salt at pH 1±0.1. The off-white product was precipitated with 2-propanol, recovered by centrifugation and dried according to a defined procedure.

As shown in numerous experiments, elevated temperatures as well as surprisingly high amounts of reducing reagent were essential for a quantitative and reproducible reduction as disulfide crosslinked chitosan-NAC polymers form hydrogels or become insoluble in aqueous systems (see Table 5).

TABLE 5

| | Reducing conditions | | |
|---|---|---|---|
| Temperature | Chitosan: NaBaH$_4$ [wt.-%] | Aqueous solution of low viscosity | Chitosan-NAC polymer No. |
| 20° C. | 1:1 | NO | 1 |
| | 1:2 | NO | 2 |
| 30° C. | 1:1 | NO | 3 |
| | 1:2 | NO | 4 |
| 40° C. | 1:1 | NO | 5 |
| | 1:2 | YES | 6 |

The only option to potentially utilize Polymers 1-5 for the manufacture of the aqueous ophthalmic solution according to this invention was to thermally degrade these disulfide crosslinked derivatives at 60° C. for more than 4 days (depending on the degree and type (inter- and intramolecular) of cross-linking) to meet the specifications in terms of kinematic viscosity of a 0.5 wt.-% aqueous solution, which is preferably in the range of 1 to 15 mm$^2$/s. In addition, the drying process is very time consuming. In contrast, the minimally crosslinked chitosan-NAC polymer No. 6 synthesized under optimized reaction conditions fell within the preferred range of the viscosity after a drying time of less than 20 hours at 60° C.

Example 7: Characterisation of Minimally Crosslinked Chitosan-NAC

Chitosan-NAC polymers Nos. 1 and 6 according to example 6 were characterised in terms of relative content of free thiol groups, molecular weight and dynamic viscosity before and after selective and quantitative reduction of any disulfides present in the final polymers with tris(2-carboxyethyl)phosphine (TCEP).

Determination of relative thiol group content: The Chitosan-NAC polymers solubilized as aqueous solutions of 1.5% (w/w) were incubated with/without TCEP (3 mg/ml) for 90 minutes at room temperature. After acidification with 1N HCl, the Chitosan-NAC polymers were repeatedly precipitated with 2-propanol and recovered by centrifugation. The residue was dissolved in distilled water followed by addition of 2,2'-Dithiodipyridine which generates a stable thione upon reaction with free thiol moieties. This tautomeric substance could be easily quantified by UV analysis at 343 nm.

Measurement of dynamic viscosity: The Chitosan-NAC polymers solubilized as aqueous solutions of 0.5% (w/w) were incubated with/without TCEP (2 mg/ml) for 90 minutes at room temperature. Rheological characterization was done via rotational measurement at constant shear rate of 5 s$^{-1}$ at 25° C.

Molecular weight measurement (SEC analysis): In order to determine the influence of the reaction conditions on the molecular weight of the chitosan backbone, an unmodified chitosan HCl salt was prepared by using the identical reaction conditions for the synthesis of polymer 6 as described in example 6 but without the addition of the active ester of N'S-diacetylcysteine. The chitosan and Chitosan-NAC polymers solubilized in acetic acid 5% in a concentration of 0.1% (w/w) were incubated with/without TCEP (1 mg/ml) for 90 minutes at room temperature. Molecular weights were separated isocratically at a flow rate of 0.7 ml/min and determined by triple detection using the Viscotek TDA305 from Malvern Instruments.

Figure 4:
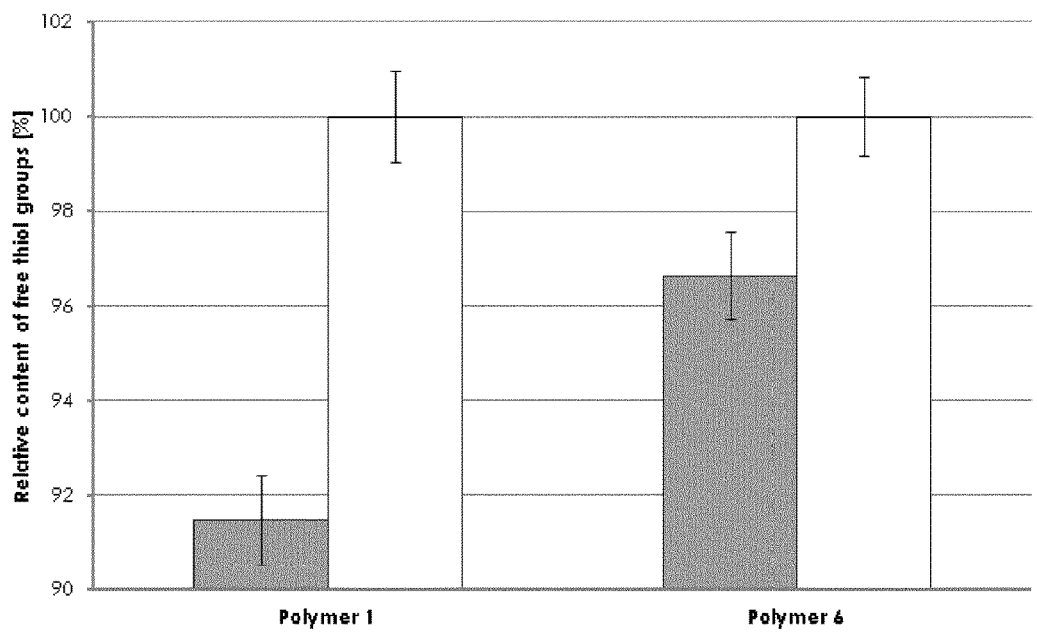
FIG. 4 shows the results of the thiol group measurements (without TCEP: grey bars, after reduction with TCEP: white bars; mean values of 3 measurements with standard deviations) of polymer 1 and polymer 6 which were synthesized as described in example 6 and analysed as described in example 7.
Figure 5:
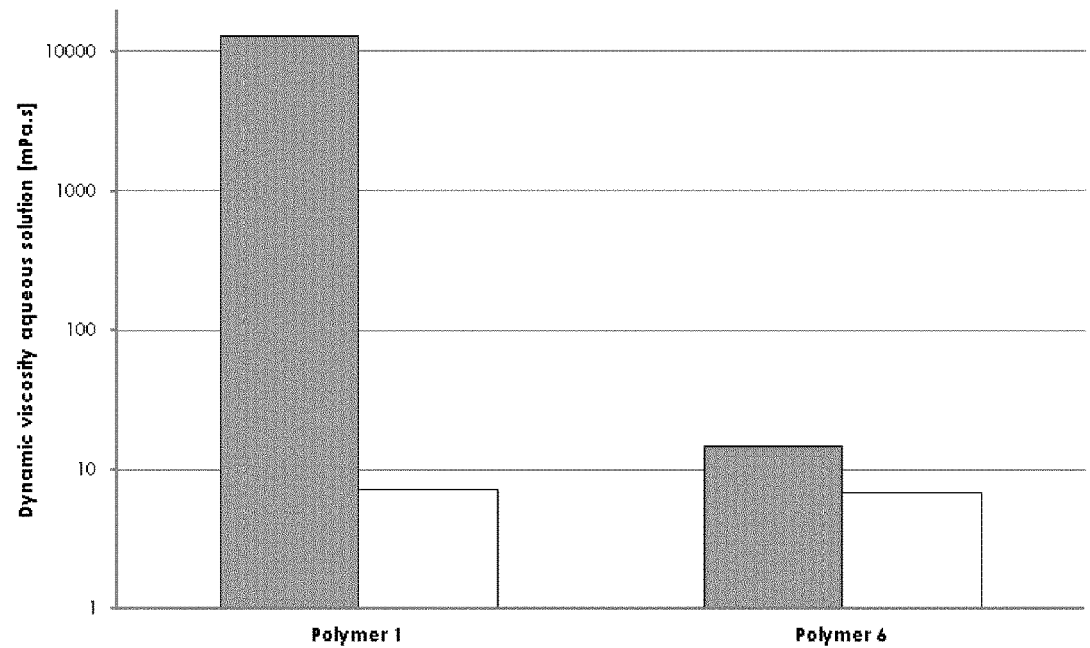
FIG. 5 shows the results of the determination of the dynamic viscosity (without TCEP: grey bars, after reduction with TCEP: white bars) of a 0.5% (w/w) solution of polymer 1 and polymer 6, which were synthesized as described in example 6 and analysed as described in example 7.

The results of the thiol group measurements of polymer 1 and polymer 6 are shown in FIG. 4 (without TCEP: grey bars, after reduction with TCEP: white bars; mean values of 3 measurements with standard deviations). The results of the determination of dynamic viscosity of a 0.5% (w/w) solution of polymer 1 and polymer 6, respectively, are shown in FIG. 5 (without TCEP: grey bars, after reduction with TCEP: white bars).

These results indicate that even the presence of a relatively small amount of disulfide crosslinked structures (9% of all N-acetylcysteine groups immobilized on the polymer in the case of polymer 1, without TCEP treatment) had a massive impact on the viscosity of chitosan-NAC polymer in an aqueous solution, whereas the minimally cross-linked chitosan-NAC with only about 3% of its thiol groups present as disulfides solubilised as aqueous solution of low viscosity which was suitable for the preparation of eye drops.

Additionally, the correlation between rheological properties of the polymers and the content of disulfide crosslinking was confirmed by SEC analysis. The minimally cross-linked chitosan-NAC polymers (polymer 6) showed a slight decrease of the molecular weight of 20-30% after quantitative reduction by TCEP. After quantitative reduction the molecular weight of polymer 6 was comparable to the molecular weight of the unmodified chitosan.HCl. The main amount of the partially cross-linked (9%) chitosan-NAC (polymer 1) however exhibited molecular weights beyond the exclusion limits of the columns and even the analyzable fraction (about 20%) yielded molecular weights four times of its initial weight. After quantitative reduction with TCEP the molecular weight of polymer 1 was in the same range as the molecular weight of the unmodified chitosan HCl. As expected, reaction of unmodified chitosan.HCl with TCEP did not result in any molecular weight decrease.

Example 8: Mucoadhesion Testing

The mucoadhesive properties of chitosan-NAC polymers with different degrees of free thiol groups were evaluated by measuring their interaction with isolated mucins. Chitosan-NAC polymers were synthesized as described in example 5 and used to prepare aqueous ophthalmic formulations as described in example 2. Unmodified chitosan.HCl was used as control.

Aqueous ophthalmic formulations containing chitosan-NAC or chitosan.HCl, respectively, were incubated at 32° C. for 30 min with aqueous solutions of isolated and cesium chloride gradient purified pig gastric mucins. The final concentration of polymer in each sample was 0.15% (w/w). Aggregates were allowed to form over night and were removed from the solution via centrifugation on the next day. After centrifugation the aggregates were resuspended in distilled water for the rheological measurements. The stability of the resulting suspensions was evaluated via oscillatory amplitude sweep tests (Rheometer MCR 101, cone-plate measuring system) at an angular frequency of 10 rad/s to determine the linear viscoelastic range.

Figure 8:
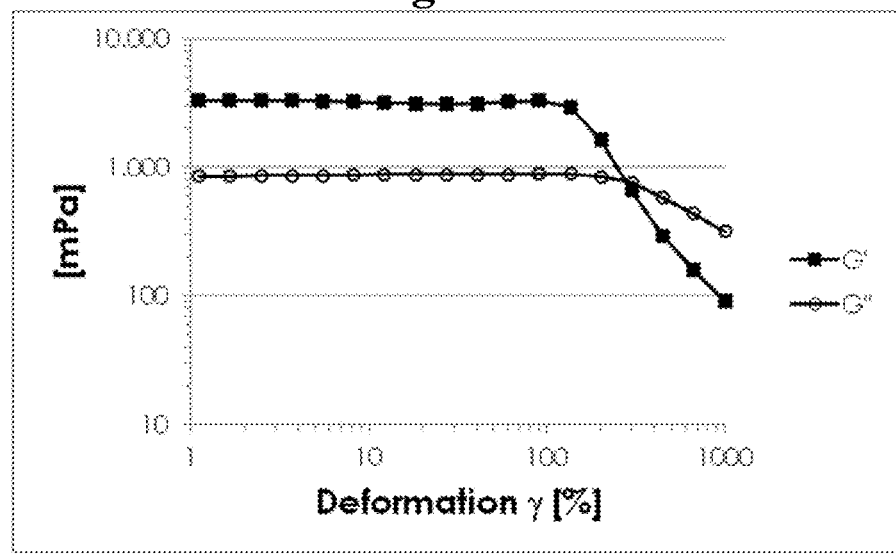

Results of this example showed that chitosan-NAC polymers with a degree of thiolation in the range of about 80 µM to 25004 per g polymer interacted strongly with the mucins as evidenced by a broad linear viscoelastic region and the large difference between the storage modulus G' and the loss modulus G". One example is shown in FIG. 8 (content of free thiol groups 80 µmol/g).

Figure 6:
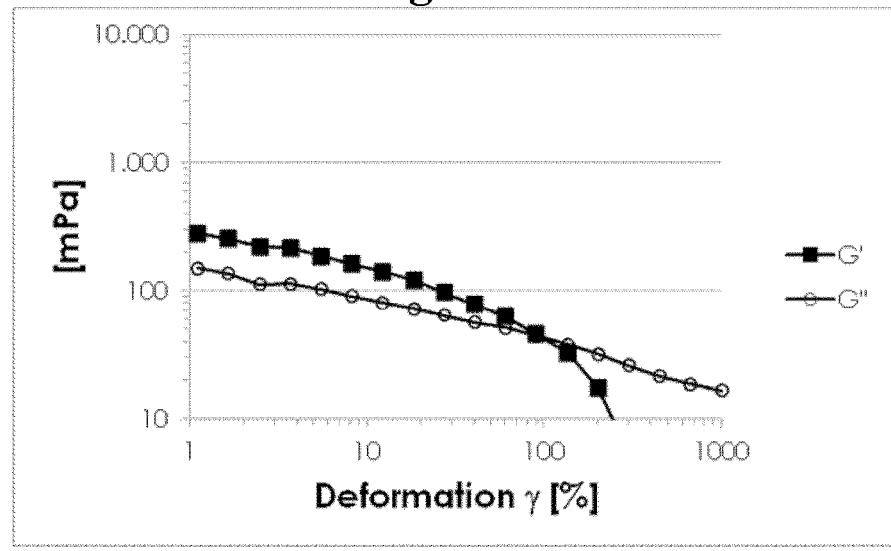
FIGS. 6, 7 and 8 show the determination of the linear viscoelastic range of a N—(N-acetylcysteinyl-)chitosan-.HCl-mucin network.
Figure 7:
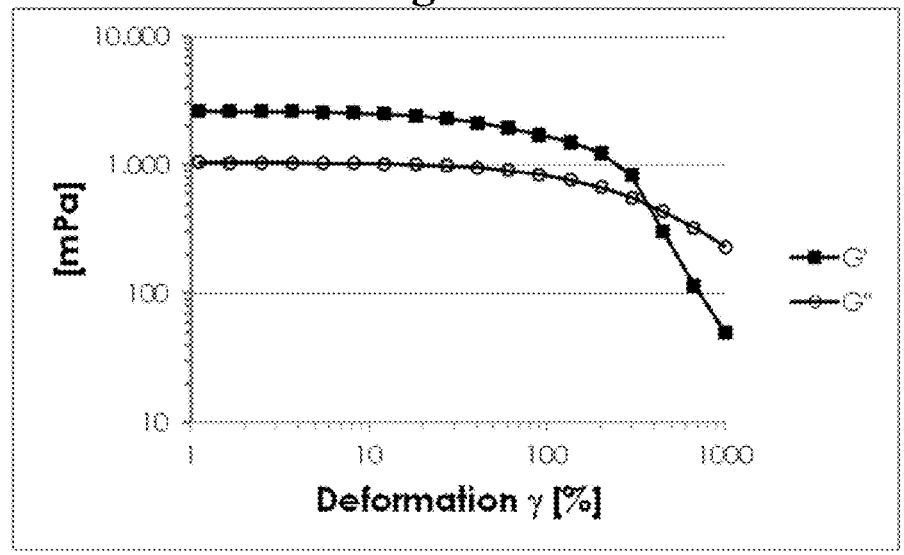

The above described effect was dependent on the degree of thiolation. Unmodified chitosan HCl and chitosan-NAC with a degree of modification of 40 µM thiol groups/g polymer showed only weak interaction with the mucins as evidenced by a non-existent and very narrow linear viscoelastic range, respectively. Results are shown in FIG. 6 (no thiolation, unmodified chitosan.HCl), FIG. 7 (content of free thiol groups 40 µmol/g) and FIG. 8 and described in Table 6. Only when the degree of thiolation was about 80 µM/g polymer the chitosan-NAC began to exhibit strong mucoadhesive properties as evidenced by strong interaction with mucins.

TABLE 6

Determination of polymer-mucin interaction strength

| Raw material | Content of free thiol groups [µmol/g thiomer] | Deformation γ (LVE range) [%] |
| --- | --- | --- |
| Chitosan•HCl | — | — |
| Chitosan-NAC | 40 | 15 |
| Chitosan-NAC | 80 | 90 |

Example 9: Determination of Ocular Residence Time of Aqueous Ophthalmic Solutions Containing 0.1% Radiolabelled Chitosan-NAC after Single Ocular Instillation in Rabbits Aim of the study was to obtain pharmacokinetic data of $^{124}$I labeled chitosan-NAC at a concentration of 0.1% (w/w) after single topical application of the test substance in a physiological buffer solution into the eye of female New Zealand white rabbits. Within this pilot study all of the four test animals received a single topical instillation of $^{124}$I-Chitosan-NAC 0.1% (w/w) into the right eye. As controls, two animals received additionally a single topical application of $^{124}$I-Chitosan-HCl 0.1% (w/w) into the left eye and the remaining two animals received buffered $^{124}$I—NaI into the left eye. Dynamic microPET measurements (350-650 keV energy window, 6 ns timing window) were performed for 1 hour after the administration of the test substances. Additionally, 15-min static scans were performed at 3, 6, and 9 hours, 30-min static scans were performed at 24 hours and 60-min static scans were performed 48, 72 and 96 hours after test substance administration. As main outcome parameter the radioactivity concentrations at the application sites were monitored. A calibration factor for converting units of microPET images into absolute radioactivity concentrations was first generated by measuring a calibration cylinder phantom filled with a known radioactivity concentration of Na$^{124}$I solution. Radioactive test substance concentration was quantified from each image using the image analysis software AMIDE2. An ellipsoidal region of interest (ROIs) was positioned at the edge of the eyes on the sagittal transmission image, whereby the area with high activity uptake located in the caruncle (inner corner of the eye) was excluded from the ROI. From the defined ROIs time-radioactivity concentration curves (TACs), which means the radioactivity concentration (µCi/g) as a function of time in the tissue defined by the ROI were calculated. The percent of applied dose per gram tissue (% AD/g) was calculated as average tissue concentration (µCi/g) divided by the totally applied radioactivity (µCi) at the start of the experiment. Area-under the curve values were calculated from the time-radioactivity concentration curves using PRISMS software (GraphPad Software, La Jolla, Calif.).

As an additional quality control parameter thiol group content in the $^{124}$I labeled chitosan-NAC solution was measured before administration.

Figure 9:
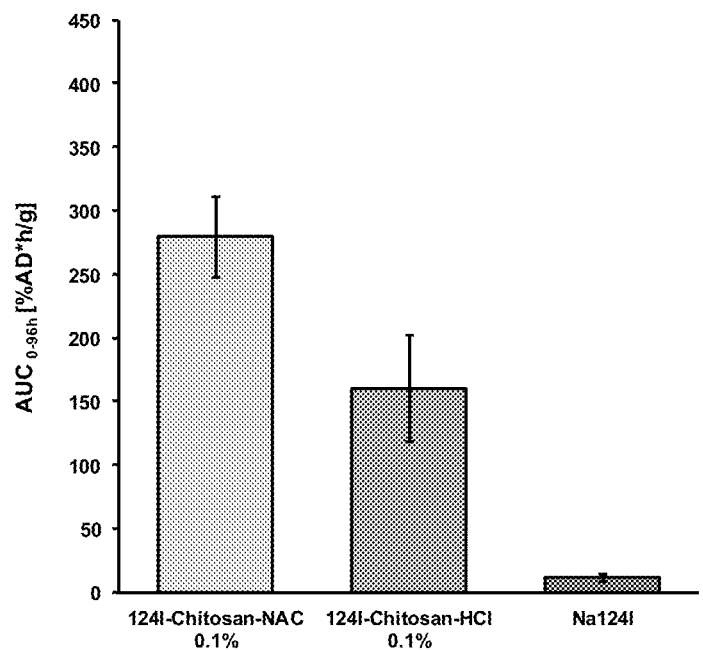
FIG. 9 shows the calculated area under the curve values (0-96 h) derived from individual time-radioactivity concentration curves of eyes treated with $^{124}$I-chitosan-NAC, $^{124}$I-chitosan.HCl and Na$^{124}$I, respectively.

Results are shown in FIG. 9. Na$^{124}$I was rapidly cleared from the eye and hardly detectable at 6 hours after application. Single administration of 0.1% (w/w) $^{124}$I-Chitosan-NAC solutions resulted in increased activity concentrations at the administered eye as compared to $^{124}$I-Chitosan-HCl indicating an increase in mucoadhesive properties. At 24 hours after administration, activity concentration in the eyes treated with 0.1% (w/w) $^{124}$I Chitosan-NAC was almost 2.2-fold higher compared to the $^{124}$I-Chitosan-HCl eyes (2.16±0.36 vs 1.21±0.26% AD/g, respectively). This difference was maintained for the next observation period so that at 48 hours after administration 2.35±0.15% AD/g ($^{124}$I-Chitosan-NAC) vs. 1.06±0.30% AD/g ($^{124}$I-Chitosan-HCl) were found. Activity concentrations for both applied test substances did then decrease and were almost comparable at 96 hours after administration.

Determination of the thiol group content for the $^{124}$I labeled chitosan-NAC solutions used for this study (two solutions prepared on two different days) showed that about 110 µM and 130 µM thiol groups/g polymer, respectively, remained in the free, i.e. unoxidized form after radiolabelling with Bolton-Hunter reagent.

Example 10: Comparison of the Ocular Residence Time of Aqueous Ophthalmic Solutions Containing 0.1% Radiolabelled Chitosan-NAC or 0.1% Radiolabelled HA-Cysteamine after Single Ocular Instillation in Rabbits In addition to the aforementioned study pharmacokinetic data were obtained for $^{124}$I-labelled Chitosan-NAC and $^{124}$I-labelled thiolated hyaluronan (HA-cysteamine) after topical application of the test substance at a concentration of 0.1% (w/w) in a physiological buffer solution into the eye of female New Zealand white rabbits. Within this study test subjects received a single topical instillation of either 0.1% (w/w) $^{124}$I-HA-cysteamine (n=3) or 0.1% (w/w) $^{124}$I-Chitosan-NAC (n=2) into the right eye while the left eye was kept untreated. Repeated microPET measurements were performed for up to 3 days (72 hours) after application of the test substances. As main study parameter the radioactivity concentrations at the application sites were monitored. Therefore, dynamic microPET measurements (350-650 keV energy window, 6 ns timing window) were performed for 1 hour after the administration of the test substances. Additionally, 15-min static scans were performed at 6 hours, 30-min static scans were performed at 24 hours, and 60-min static scans were performed 48 hours and 72 hours after test substance administration.

Figure 10:
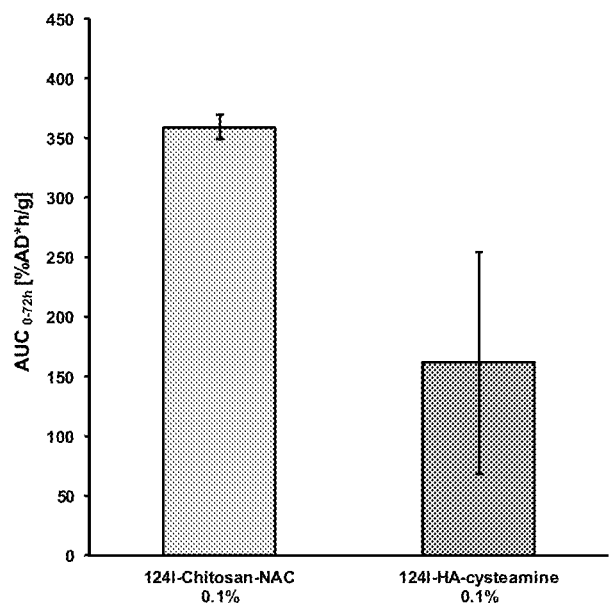
FIG. 10 shows area-under the curve (AUC) values (0-72 h) calculated from individual time-radioactivity concentration curves (% AD*h/g) of eyes treated with $^{124}$I-chitosan-NAC and $^{124}$I-labeled thiolated hyaluronan (HA-cysteamine).

Quantitative analysis of obtained microPET pictures was performed as described above and results shown in FIG. 10 are given as area-under the curve (AUC) values calculated from the time-radioactivity concentration curves (% AD*h/g). Determination of the thiol group content in the $^{124}$I labelled chitosan-NAC and $^{124}$I-HA-cysteamine solutions used for this study showed that about 154 µM and 54 µM thiol groups/g polymer, respectively, remained in the free, i.e. unoxidized form after radiolabelling.

Example 11: Comparison of the Pharmacokinetic Behaviour of $^{124}$I Labeled Chitosan-NAC Solutions after Single Ocular Instillation in Rabbits The ocular distribution of $^{124}$I labeled chitosan-NAC solutions containing $^{124}$I labeled chitosan-NAC in concentrations of 0.05%; 0.1%; 0.3% and 0.5% (w/w), respectively, after a single instillation was evaluated via qualitative assessment of microPET Scan projection images of summed data at different time points. The results are listed in Table 7.

TABLE 7

Qualitative assessment of the ocular distribution of 4 different radioactive labeled chitosan-NAC solutions

| Concentration (% w/w) of $^{124}$I labeled chitosan-NAC in the ophthalmic test solution | Qualitative assessment t = 0-1 h | Qualitative assessment t = 6 h | Qualitative assessment t = 22-24 h |
|---|---|---|---|
| 0.05% | Even distribution on ocular surface, notable accumulation in tear duct (clearance) | Even distribution on ocular surface; clear reduction of activity as compared to t = 0-1 | Not determined |
| 0.1% | Even distribution on ocular surface, some accumulation in tear duct (clearance) | Even distribution on ocular surface | Even distribution on ocular surface |
| 0.3% | Even distribution on ocular surface | Even distribution on ocular surface | Even distribution on ocular surface |
| 0.5% | uneven distribution on ocular surface with highest radioactivity concentrations in conjunctival sac and inner canthus of the eye | Uneven distribution on ocular surface with highest radioactivity concentrations in conjunctival sac and inner canthus of the eye; clearly reduced activity compared to 0.3% test solution at the same time point | Uneven distribution on ocular surface with highest radioactivity concentrations in conjunctival sac and inner canthus of the eye; reduced activity compared to 0.3% test solution at the same time point |

The qualitative assessment of ocular surface distribution of 4 different radioactive labelled chitosan-NAC solutions clearly showed that solutions with concentrations of 0.1% and 0.3% chitosan-NAC showed the best results regarding even distribution on the ocular surface of rabbits for 24 h. The solution containing 0.05% was cleared more rapidly from the ocular surface. The solution containing 0.5% chitosan-NAC was not as evenly distributed on the eye and also was cleared more rapidly from the ocular surface.

Example 12: Effect of Chitosan-NAC on Tear Film Thickness in Patients with Dry Eye Syndrome The aim of this study was to investigate the effect of eye drops containing 0.1% chitosan-NAC (171 µmol/g free thiol groups) on tear film thickness in patients with dry eye syndrome after a single dose and after 5 day treatment. For this purpose 2 cohorts were planned: In Cohort I, chitosan-N-acetylcysteine eye drops were instilled once in one randomly chosen eye, whereas the fellow eye received placebo. Measurements of tear film thickness were performed with optical coherence tomography (OCT) before instillation and 10 minutes, 1 hour, 2 hours, 4 hours, 8 hours, 10 hours, 12 hours and 24 hours after instillation. The results (median tear film thickness in µm, range in parentheses, n=16) are shown in Table 8.

TABLE 8

Results of tear film thickness measurements of cohort I

| Time | Chitosan-NAC | Placebo |
|---|---|---|
| pre-dose | 3.9 (3.3-4.8) | 4.0 (3.0-5.3) |
| 10 min | 4.7 (3.4-7.0) | 4.2 (2.0-6.3) |
| 8 h | 4.7 (3.5-6.5) | 4.2 (3.0-6.5) |
| 10 h | 5.2 (3.5-7.9) | 4.3 (3.3-5.5) |

TABLE 8-continued

Results of tear film thickness measurements of cohort I

| Time | Chitosan-NAC | Placebo |
|---|---|---|
| 12 h | 4.6 (3.7-7.6) | 4.1 (2.9-6.9) |
| 24 h | 4.7 (4.0-8.1) | 4.7 (2.8-6.3) |

In Cohort II, 16 Patients were randomized to receive chitosan-NAC eye drops 0.1% once a day in the right eye and twice a day in the left eye or vice versa. The other eye received placebo for the second instillation. Measurements of tear film thickness with OCT were performed every study day before the morning instillation and the day after the last instillation. The Ocular Surface Disease Index (OSDI) was assessed as secondary efficacy variable in cohort II at screening and at day 6.

The results of tear film thickness measurements in cohort II are shown in Table 9 (median tear film thickness (μm) of "once daily" and "twice daily" group in Cohort II; range in parentheses, n=16).

TABLE 9

Results of tear film thickness measurements of cohort II

| Study Day | twice daily (BID) | once daily (QD) |
|---|---|---|
| 1 | 3.7 (2.7-6.1) | 3.4 (2.8-6.0) |
| 2 | 4.3 (2.7-6.6) | 3.9 (2.7-7.5) |
| 3 | 4.1 (3.0-7.4) | 3.9 (2.9-8.5) |
| 4 | 4.3 (2.7-6.9) | 4.1 (2.5-7.2) |
| 5 | 4.4 (2.9-7.7) | 4.1 (3.3-8.4) |
| 6 | 4.4 (3.3-7.3) | 4.0 (2.9-7.2) |

Based on a regression analysis over the entire 24 hr post-dose period, the increase in tear film thickness was statistically significant if the treatment group of cohort I was compared with the placebo group (Regression analysis to identify between-treatment differences over time, p<0.0001). These results show that chitosan-NAC eye drops caused a statistically significant increase of tear film thickness over a time period of 24 h, suggesting a long corneal residence time. Tear film thickness was restored to a level found in healthy subjects (Werkmeister, Alex et al., 2013, Measurement of tear film thickness using ultrahigh-resolution optical coherence tomography, Invest Ophthalmol Vis Sci (54): 5578-5583). In cohort II once daily instillations were sufficient to restore tear film thickness and were not inferior to twice daily applications.

In Cohort II the median ocular surface disease index at screening was 38.5 and improved to 13.0 at day 6, which corresponds to a decrease by 60.5%. This indicates that the subjective severity of DES as assessed with the OSDI improved after five days of treatment with chitosan-NAC eye drops 0.1%.

What is claimed is:

1. A sterile aqueous ophthalmic solution comprising:
   a carrier solution; and
   0.05% to 0.5% (w/w) of N—(N-acetylcysteinyl-)chitosan or a pharmaceutically acceptable salt thereof in the carrier solution,
   wherein the N—(N-acetylcysteinyl-)chitosan or pharmaceutically acceptable salt thereof has a content of free thiol groups in an amount of from 80 μmol/g polymer to 280 μmol/g polymer.

2. The ophthalmic solution according to claim 1, wherein the concentration of the N—(N-acetylcysteinyl-)chitosan or pharmaceutically acceptable salt thereof in said solution is from 0.05 to 0.3% (w/w).

3. The ophthalmic solution according to claim 1, wherein the N—(N-acetylcysteinyl-)chitosan is provided as a pharmaceutically acceptable salt.

4. The ophthalmic solution according to claim 1, wherein the N—(N-acetylcysteinyl-)chitosan or pharmaceutically acceptable salt thereof has a content of free thiol groups in an amount of from 105 μmol/g polymer to 250 μmol/g polymer.

5. The ophthalmic solution according to claim 1, wherein the N—(N-acetylcysteinyl-)chitosan or pharmaceutically acceptable salt thereof has a content of crosslinked thiol groups that is 30% or less of total thiol groups therein.

6. The ophthalmic solution according to claim 1, further comprising at least one excipient selected from the group consisting of boric acid, salts of boric acid, salts of citric acid, salts of acetic acids, polyethylene glycol, Na$_2$-EDTA, mannitol, sorbitol, gylcerol, sodium chloride, sodium metabisulfite, hydroxypropyl methylcellulose, polyvinylpyrrolidone, polyvinylalcohol, lubricin, hyaluronic acid, pharmaceutically acceptable salts of hyaluronic acid, and mixtures thereof.

7. The ophthalmic solution according to claim 6, comprising:
   0.05% to about 0.5% (w/w) of N—(N-acetylcysteinyl-)chitosan or pharmaceutically acceptable salt thereof;
   Boric acid in an amount from 1.0 to 16.0 mg/ml;
   Polyethylenglycol 400 in an amount from 0.01 to 5.0 mg/ml;
   Na$_2$-EDTA in an amount from 0.01 to 0.5 mg/ml;
   Mannitol in an amount from 0.01 to 5.5 mg/ml;
   Sodium chloride in an amount from 0.01 to 9 mg/ml; and
   Hydroxypropyl methylcellulose in an amount from 0.01 to 20 mg/ml.

8. The ophthalmic solution according to claim 1, wherein the N—(N-acetylcysteinyl-)chitosan or pharmaceutically acceptable salt thereof used for the preparation of the solution exhibits at a concentration of 0.5% in water at 25° C. a kinematic viscosity within the range of 1 to 15 mm$^2$/s.

9. The ophthalmic solution according to claim 1, wherein the solution exhibits an osmotic pressure of from 150 to 400 mOsM.

10. The ophthalmic solution according to claim 1, wherein the solution exhibits a pH-value of from 5.8 to 6.8.

11. A kit comprising a container and an ophthalmic solution according to claim 1 in an essentially oxygen-free atmosphere.

12. The kit according to claim 11, comprising a first container containing the ophthalmic solution and a second container containing said first container.

13. The kit according to claim 12, wherein said container and/or said first container and/or said second container is/are in the form a gas tight sachet.

14. The kit according to claim 13, wherein said gas tight sachet contains one or more single dose sub-containers containing said ophthalmic solution.

15. The kit according to claim 12, wherein said container and/or said first container and/or said second container contains an oxygen absorbing material.

16. The kit according to claim 11, wherein said N—(N-acetylcysteinyl-)chitosan or pharmaceutically acceptable salt thereof contained therein has a content of free thiol groups of from about 80 μmol/g polymer to 250 μmol/g polymer after being stored for at least 12 months at room temperature.

17. The kit according to claim 11, wherein the N—(N-acetylcysteinyl-)chitosan or pharmaceutically acceptable salt thereof has a content of crosslinked thiol groups that is 30% or less of the total thiol groups therein after being stored for at least 12 months at room temperature.

* * * * *